(12) United States Patent
Mensinger et al.

(10) Patent No.: US 12,214,173 B2
(45) Date of Patent: Feb. 4, 2025

(54) INJECTION PENS FOR MEDICINE ADMINISTRATION AND TRACKING

(71) Applicant: Medtronic MiniMed, Inc., Northridge, CA (US)

(72) Inventors: Michael R. Mensinger, San Diego, CA (US); Ellis Garai, Woodland Hills, CA (US); Eric A. Larson, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 850 days.

(21) Appl. No.: 17/342,435

(22) Filed: Jun. 8, 2021

(65) Prior Publication Data

US 2022/0387720 A1    Dec. 8, 2022

(51) Int. Cl.
*A61M 5/315* (2006.01)
*A61M 5/24* (2006.01)
*A61M 5/31* (2006.01)

(52) U.S. Cl.
CPC .......... *A61M 5/31528* (2013.01); *A61M 5/24* (2013.01); *A61M 5/3146* (2013.01); *A61M 5/31515* (2013.01); *A61M 5/31568* (2013.01); A61M 2005/31588 (2013.01); A61M 2205/3306 (2013.01); A61M 2205/3317 (2013.01); A61M 2205/332 (2013.01); A61M 2205/3327 (2013.01)

(58) Field of Classification Search
CPC .. A61M 5/31528; A61M 5/24; A61M 5/3146; A61M 5/31515; A61M 5/31568; A61M 2005/31588; A61M 2205/3306; A61M 2205/332

See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |

(Continued)

*Primary Examiner* — Tasnim Mehjabin Ahmed
(74) *Attorney, Agent, or Firm* — Carter, DeLuca & Farrell LLP (57) ABSTRACT

A medicine injection pen includes a body, a drive member within the body and configured to move relative thereto upon actuation, a cartridge housing releasably engageable with the body and configured to retain a medicine cartridge, at least one sensor, and at least one detector. The medicine cartridge has a liquid medicine therein and includes a piston configured to slide therein. The drive member is configured to move relative to the body to urge the piston to slide within the medicine cartridge to dispense at least some of the liquid medicine from the medicine cartridge. The sensor(s) is configured to sense movement of the drive member relative to the body to enable determination of an amount of the liquid medicine dispensed. The detector(s) is configured to detect a gap between the drive member and the piston.

15 Claims, 10 Drawing Sheets

(56) References Cited

U.S. PATENT DOCUMENTS

| | | |
|---|---|---|
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 10,835,727 B2 | 11/2020 | Montalvo et al. |
| 2001/0034506 A1* | 10/2001 | Hirschman ........ A61M 5/14546 604/207 |
| 2005/0148938 A1* | 7/2005 | Blomquist ........ A61M 5/14244 604/152 |
| 2007/0123819 A1 | 5/2007 | Mernoe et al. |
| 2010/0160861 A1 | 6/2010 | Causey, III et al. |
| 2014/0188075 A1* | 7/2014 | Eggert ................... A61M 5/20 604/506 |
| 2015/0320934 A1* | 11/2015 | Draper .................... G01D 5/32 604/154 |
| 2018/0043104 A1* | 2/2018 | Mueller-Pathle ... A61M 5/2466 |
| 2020/0327973 A1 | 10/2020 | Pryor et al. |
| 2023/0090661 A1* | 3/2023 | Jensen .................... A61M 5/24 604/113 |

* cited by examiner

INJECTION PENS FOR MEDICINE ADMINISTRATION AND TRACKING

FIELD

The present disclosure relates to medicine administration and tracking and, more specifically, to reusable injection pens including replaceable cartridge to facilitate medicine administration and tracking.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed by the user, e.g., using a syringe, a medicine delivery pen, or a pump. Regardless of the particular device utilized for injecting the liquid medicine, it is important to accurately track the medicine dosed, particularly for managing lifelong or chronic conditions like diabetes.

SUMMARY

To the extent consistent, any of the aspects and features detailed herein can be utilized with any of the other aspects and features detailed herein in any suitable combination.

Provided in accordance with aspects of the present disclosure is a medicine injection pen including a body, a drive member disposed within the body and configured to move relative to the body upon actuation of the drive member, a cartridge housing releasably engageable with the body, one or more sensors, and one or more detectors. The cartridge housing is configured to retain a medicine cartridge therein. The medicine cartridge is configured to retain a liquid medicine therein and includes a piston configured to slide within the medicine cartridge. The drive member is configured to move relative to the body upon actuation thereof to urge the piston to slide within the medicine cartridge to thereby dispense at least some of the liquid medicine through a dispensing end of the medicine cartridge. The sensor(s) is configured to sense movement of the drive member relative to the body upon actuation of the drive member to enable determination of an amount of the liquid medicine dispensed based on the sensed movement. The detector(s) is configured to detect a gap between the drive member and the piston.

In an aspect of the present disclosure, the detector(s) is configured to detect the gap by determining whether the drive member and the piston are sufficiently approximated or in abutment with one another.

In another aspect of the present disclosure, the detector(s) is configured to detect the gap by determining a distance between the drive member and the piston.

In still another aspect of the present disclosure, the detector(s) is configured to detect the gap by sensing a force required to move the drive member.

In yet another aspect of the present disclosure, the detector(s) is configured to detect the gap by determining a position of the piston. In such aspects, the detector(s) may be configured to detect the gap by determining a position of the piston based on an amount of the liquid medicine in the medicine cartridge. The position of the piston, in aspects, is determined relative to at least one of: the body, the drive member, or the medicine cartridge.

In still yet another aspect of the present disclosure, the detector(s) includes at least one of: a contact sensor, a magnet sensor, an optical sensor, a proximity sensor, a force sensor, an RFID sensor, or an NFC sensor.

In another aspect of the present disclosure, the drive member is a drive screw configured to rotate and translate relative to the body to urge the piston to slide. In such aspects, the sensor(s) may be configured to sense rotation of the drive screw to enable determination of the amount of the liquid medicine dispensed.

In yet another aspect of the present disclosure, the pen includes an electronics unit configured to output an indication based upon whether the gap is detected. The indication may indicate at least one of: that the pen is ready for use, that the pen requires priming, that the pen requires adjustment, or that there is an error.

In another aspect of the present disclosure, the pen includes an electronics unit configured to determine the amount of the liquid medicine dispensed based on the sensed movement. In such aspects, the electronics unit may be configured to determine the amount of the liquid medicine dispensed based on the sensed movement and a distance of the gap.

In still another aspect of the present disclosure, the sensor(s) includes an encoder.

In another aspect of the present disclosure, the detector(s) is further configured to detect information relating to the medicine cartridge.

Another medicine injection pen provided in accordance with the present disclosure includes a body, a drive member disposed within the body and configured to move relative to the body upon actuation of the drive member, a cartridge housing releasably engageable with the body, and one or more detectors. The cartridge housing is configured to retain a medicine cartridge therein. The medicine cartridge is configured to retain a liquid medicine therein. The drive member is configured to move relative to the body upon actuation thereof to dispense at least some of the liquid medicine through a dispensing end of the medicine cartridge. The detector(s) is configured to detect whether the cartridge housing is properly engaged with the body.

In an aspect of the present disclosure, the detector(s) is configured to detect whether the cartridge housing is properly engaged with the body by determining whether the drive member and the medicine cartridge are sufficiently approximated or in abutment with one another.

In another aspect of the present disclosure, the detector(s) is configured to detect whether the cartridge housing is properly engaged with the body by determining whether the body and the cartridge housing are sufficiently approximated or in abutment with one another.

In another aspect of the present disclosure, the detector(s) is configured to detect whether the cartridge housing is properly engaged with the body by determining whether the body and the medicine cartridge are sufficiently approximated relative to one another.

DETAILED DESCRIPTION

Figure 1A:
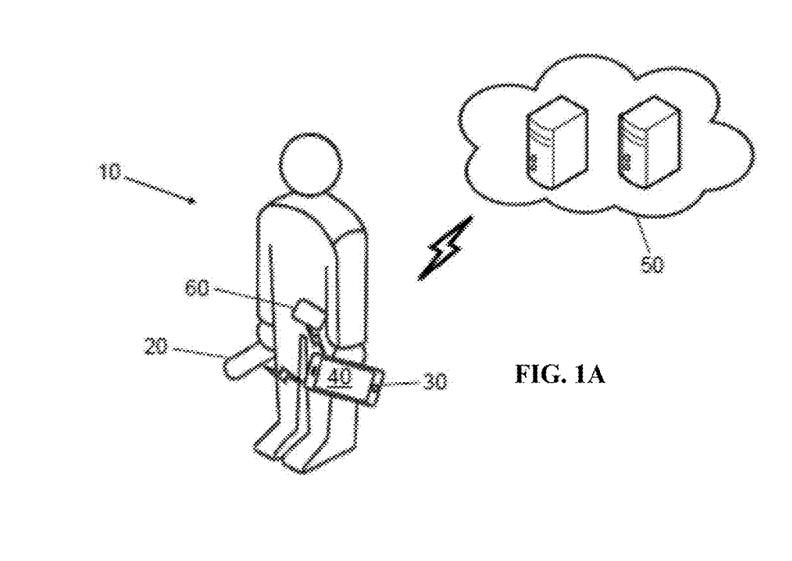
FIG. 1A is a schematic illustration of a medicine administration and tracking system provided in accordance with the present disclosure including a medicine injection pen, a computing device, and, in aspects, a sensor device and/or a data processing system.

FIG. 1A illustrates a medicine administration and tracking system 10 provided in accordance with the present disclosure including a medicine injection pen 20 in wireless communication with a computing device 30 running a health management application 40 associated with pen 20 and/or other devices part of or connected to system 10. System 10, in aspects, further includes a data processing system 50 and/or a sensor device 60. While the reusable injection pens with replaceable cartridges of the present disclosure are detailed herein configured for use as medicine injection pen 20 of system 10 with respect to diabetes management, it is understood that the reusable injection pens of the present disclosure are also applicable to management of other diseases and medical conditions and/or for use with other medicine administration and tracking systems.

Medicine injection pen 20, described in greater detail below, is a reusable injection pen configured to removably receive a medicine cartridge, e.g., a cartridge of insulin, for injecting a selected dose of insulin into a patient and recording information concerning the injected dose of insulin, e.g., a dose amount and/or timestamp data associated with the dose.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc.

Health management application 40 is paired with pen 20, which may be a prescription-only medical device, via smartphone 30, although other suitable configurations are also contemplated. In aspects, the pairing of smartphone 30 with pen 20 at least partially unlocks health management application 40 to enable the user to utilize some or all features of health management application 40, e.g., according to the user's prescription. Thus, the act of pairing can unlock and enable the functionality of health management application 40 and/or system 10 (including pen 20), while health management application 40 (and/or system 10) may provide only limited features in the absence of pairing with pen 20.

Health management application 40 of smartphone 30, in aspects, can monitor and/or control functionalities of pen 20 and provide a dose calculator module and/or decision support module that can calculate and recommend a dose of medicine for the user to administer using pen 20. Health management application 40 provides a user interface, on the user interface of smartphone 30, to allow a user to manage health-related data. For example, health management application 40 can be configured to control some functionalities of pen 20 and/or to provide an interactive user interface to allow a user to manage settings of pen 20 and/or settings for smartphone 30 that can affect the functionality of system 10 (FIG. 1A). Smartphone 30 can additionally or alternatively be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface, to guide and aid the user in monitoring their condition, using pen 20, and/or managing their behavior to promote treatment and better health outcomes.

In aspects, system 10 further includes a data processing system 50 in communication with pen 20 and/or smartphone 30. Data processing system 50 can include one or more computing devices in a computer system and/or communication network accessible via the internet, e.g., including servers and/or databases in the cloud. System 10 can additionally or alternatively include sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores, and displays the continuous glucose values for the user. Such continuous glucose values can be utilized by health management application 40, for example, for displaying health data, in dose calculation and/or decision support, etc.

Figure 1B:
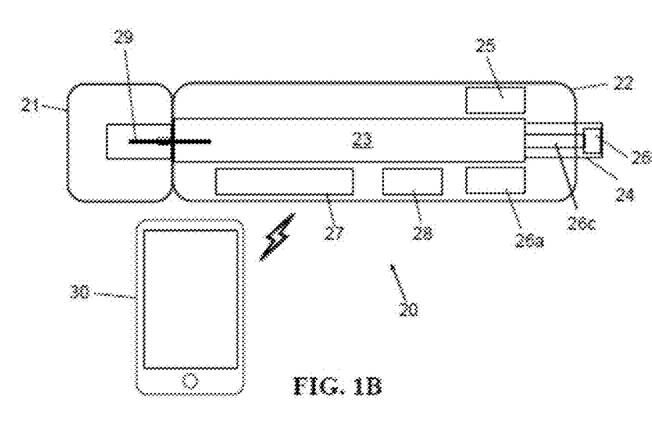
FIG. 1B is a block diagram of the medicine injection pen of the system of FIG. 1A.

With reference to FIG. 1B, pen 20 includes a cap 21 configured to protect a medicine dispensing element (e.g., a needle 29) and a body 22 configured to contain a replaceable medicine cartridge 23, e.g., an insulin cartridge. Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); and an electronics unit 27 that can include a processor, a memory, a transceiver, and a battery or other suitable power source.

In aspects, in order to operate pen 20, the user first sets e.g., dials, a dose using a dose knob 26a of dose setting mechanism 25. For example, the dose may be adjusted up or down to achieve a desired dose amount prior to administration of the dose by rotating dose knob 26a in an appropriate direction. Once the appropriate dose has been set, the user applies a force against a dose dispensing button 26b of dose dispensing mechanism 24 to begin dispensing. More specifically, to begin dispensing, the user presses against the portion of dose dispensing button 26b that protrudes from body 22 of pen 20 to thereby drive a driving element 26c, e.g., a drive screw 26c, of dose dispensing mechanism 24 against an abutment, e.g., piston 23b (FIG. 2B), of medicine cartridge 23 to dispense an amount of medicine from cartridge 23 through needle 29 into the user in accordance with the dose amount set by dose setting mechanism 25, e.g., dose knob 26a, during setting.

Operations monitoring mechanism 28 of pen 20 senses movement of a rotating and/or translating driving component (e.g., drive screw 26c (see also FIG. 2B)) of dose dispensing mechanism 24. Operations monitoring mechanism 28 may include one or more switches, sensors, and/or encoders for this purpose. More specifically, any suitable switch(es), sensor(s), and/or encoder(s) may be utilized to sense rotary and/or linear movement. Non-limiting examples of such include rotary and linear encoders, Hall effect and other magnetic-based sensors (e.g., magnetic field sensors, magnetic polar sensors, etc.), linearly variable displacement transducers, optical sensors, etc. With respect to an encoder, for example, the encoder can be configured to sense the rotation of drive screw 26c (FIG. 2B) that, in turn, translates to dispense medicine; thus, by sensing rotation of drive screw 26c (FIG. 2B), the translational movement of drive screw 26c can be readily determined. Movement of the encoder may be detected as data processed by the processor of electronics unit 27 of pen 20, from which the amount of medicine dosed can be determined.

In aspects, the processor of electronics unit 27 of pen 20 can store the dose along with a timestamp for that dose and/or any other information associated with the dose. In aspects, the transceiver of electronics unit 27 enables pen 20 to transmit the dose and related information to smartphone 30. In such aspects, once the dose is transmitted, the dose data and any related information associated with that particular transmitted dose is marked in the memory of electronics unit 27 of pen 20 as transmitted. If the dose is not yet transmitted to smartphone 30 such as, for example, because no connection between the pen 20 and smartphone 30 is available, then the dose and associated data can be saved and transmitted the next time a successful communication link between pen 20 and smartphone 30 is established.

The timestamp may be the current time or a time from a count-up timer. When the dose and associated information is communicated to health management application 40 running on smartphone 30, the timestamp and/or "time-since-dose" parameter (as determined by the count-up timer) is transmitted by pen 20 and received by smartphone 30 for storage in memory 33 of data processing unit 31 of the smartphone 30 (see FIG. 1C). Where a count-up timer is utilized, the time of the dose can be determined without pen 20 having to know the current time, which can simplify operation and setup of pen 20. That is, health management application 40 can determined the time of dose based on the current time and the value returned from the count-up timer.

Dose dispensing mechanism 24 of pen 20 can include a manually powered mechanism (user powered and/or mechanically biased), a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to drive screw 26c of dose dispensing mechanism 24, drive screw 26c turn provides a force to urge medicine from medicine cartridge 23 to deliver the set or dialed dose. In aspects, dose dispensing mechanism 24 can be operated such that rotation and/or translation of the driving element, e.g., drive screw 26c, is facilitated by a variable tension spring or a variable speed motor to inject the dose over a specific time frame (e.g., 1 s, 5 s, etc.) to help reduce the pain of dosing and/or for other purposes.

Figure 1C:
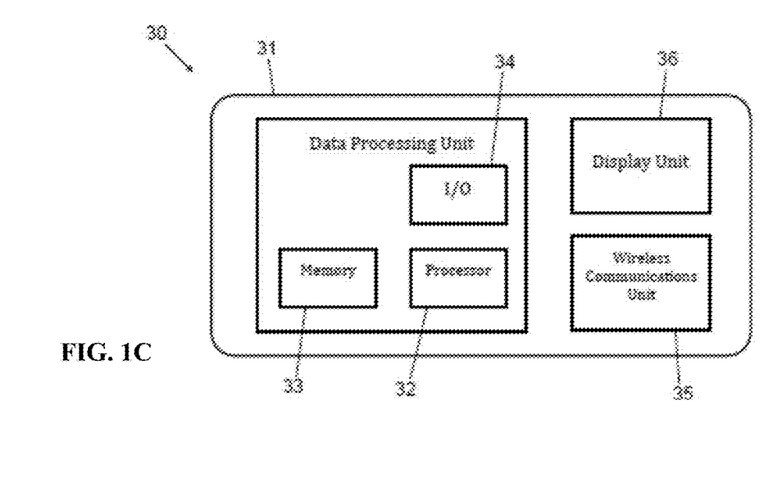
FIG. 1C is a block diagram of the computing device of the system of FIG. 1A.

FIG. 1C illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Once smartphone 30 receives the dose and related information (e.g., which can include time information, dose setting, and/or dose dispensing information, and other information about pen 20 and/or the environment as it relates to a dosing event), smartphone 30 stores the dose related information in memory 33, e.g., which can be included among a list of doses or dosing events. In aspects, via the user interface associated with health management application 40, smartphone 30 allows the user to browse a list of previous doses, to view an estimate of current medicine active in the patient's body (medicine on board, e.g., insulin on board) based on calculations performed by health management application 40, and/or to utilize a dose calculation module to assist the patient regarding dose setting information on the size of the next dose(s) to be delivered. For example, the patient may enter carbohydrates to be eaten and current blood sugar (which alternatively may be obtained directly from sensor device 60 (FIG. 1A)), and health management application 40 may already know insulin on board. Using these parameters, a suggested medicine dose (e.g., a recommended insulin dose), calculated by the dose determination module, may be determined. In aspects, smartphone 30 can also allow the user to manually enter dose data, e.g., boluses, which may be useful if the battery in pen 20 has been depleted or another medicine delivery device, e.g., a syringe, was utilized to dose.

Figure 2A:
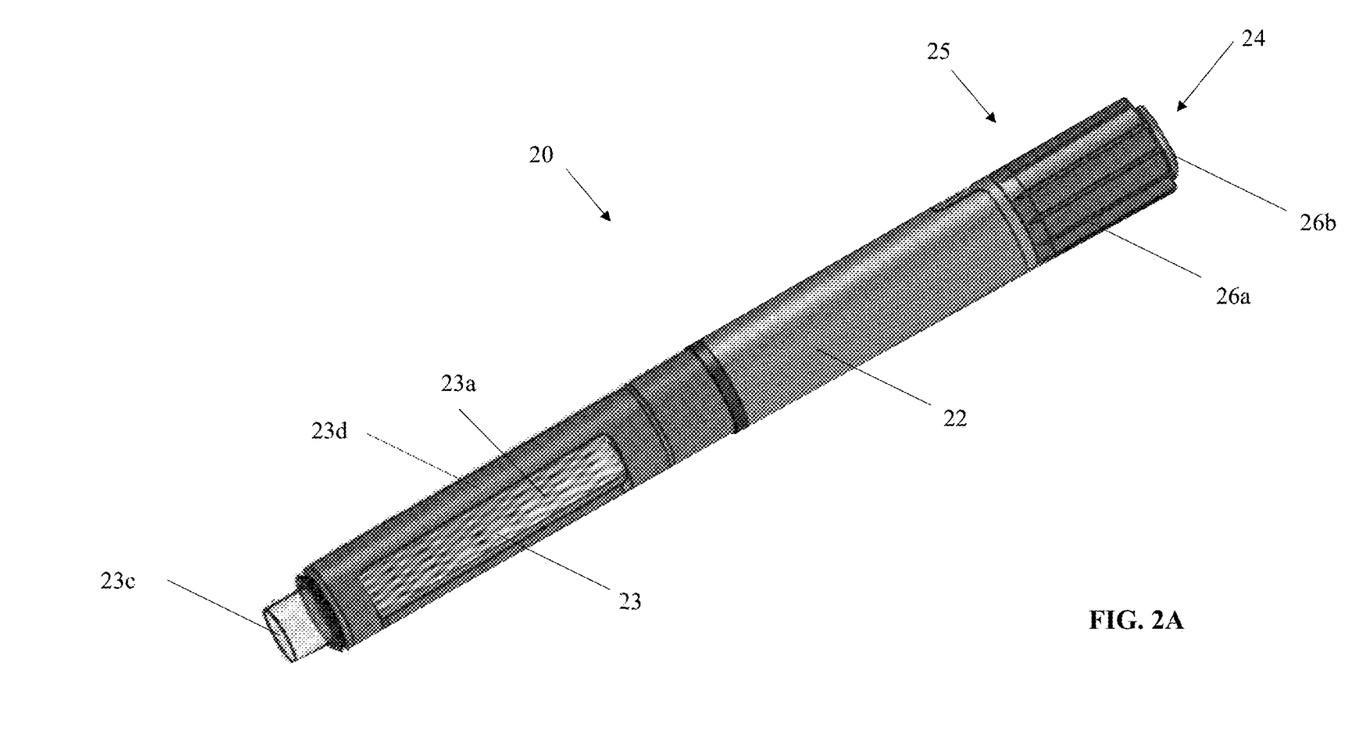
FIGS. 2A and 2B are perspective and longitudinal, cross-sectional views, respectively, of the medicine injection pen of FIG. 1B.
Figure 2B:
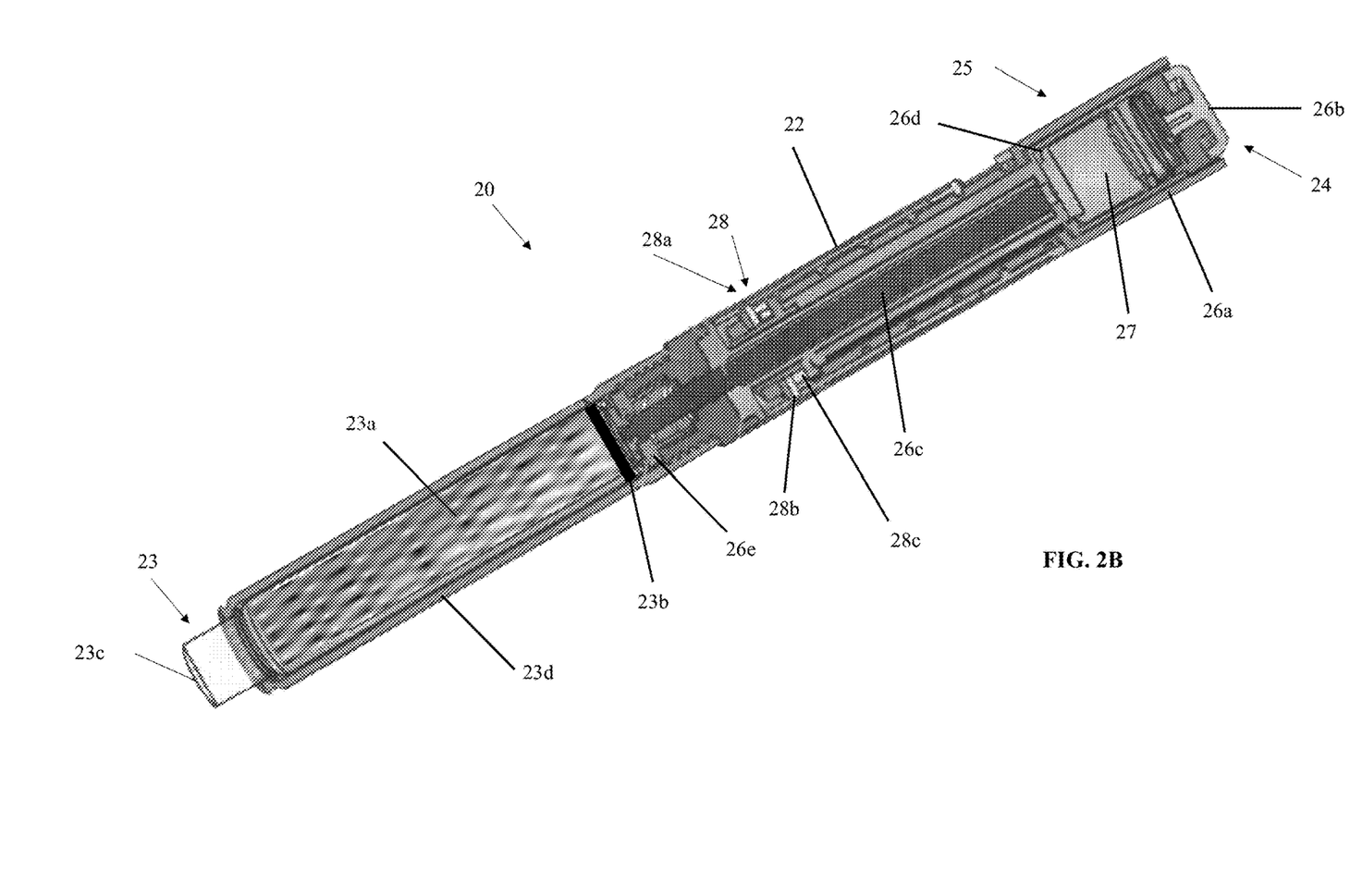

Referring to FIGS. 2A and 2B, pen 20 and, in particular, the mechanical and hardware features thereof, is detailed, although other mechanical and hardware configurations of pen 20 are also contemplated. Pen 20 is shown configured as a reusable device for use with replaceable medicine cartridge 23 which, once emptied (or for other purposes), can be replaced with another medicine cartridge 23 or refilled and reinstalled for subsequent use. Medicine cartridge 23 includes a vial body 23a defining an interior volume configured to retain a volume of medicine, e.g., insulin, therein, and a piston 23b sealingly and slidingly disposed within vial body 23a such that displacement of piston 23b within vial body 23a towards the dispensing end of vial body 23a forces medicine from the interior volume through dispensing opening 23c of cartridge 23 and needle 29 (FIG. 1B) for injection into the user. As can be appreciated, the displacement distance of piston 23b is proportional to the amount of medicine dispensed.

Medicine cartridge 23 is held within a cartridge housing 23d of pen 20 and, in aspects, may be seated within a corresponding cartridge adapted (not shown) positionable within cartridge housing 23d to enable use of various different medicine cartridges (e.g., of different size, shape, manufacturer, etc.) with pen 20. Cartridge housing 23d is releasably engageable with body 22 of pen 20, e.g., via threaded engagement, such that, when cartridge housing 23d is disengaged from body 22 of pen 20, medicine cartridge 23 can be removed and replaced and such that, when cartridge housing 23d is engaged with body 22 of pen 20 with a medicine cartridge 23 therein, medicine cartridge 23 is operably positioned relative to dose dispensing mechanism 24 of pen 20. However, other suitable configurations enabling removal and replacement of a medicine cartridge 23 are also contemplated.

Continuing with reference to FIGS. 2A and 2B, dose knob 26a of pen 20 may be coupled to body 22 of pen 20 in threaded engagement via corresponding threads defined on an exterior surface of a portion of dose knob 26a and an interior surface of a portion of body 22. In aspects, electronics unit 27 may reside within an electronics housing disposed or defined within dose knob 26a and be coupled thereto via a locking mechanism 26d (e.g., a catch-protrusion mechanism, a clutch, etc.) such that, when dose knob 26a is rotated into or out of body 22 to select or adjust the dose to be injected, electronics unit 27 remains stationary (e.g., wherein the locking mechanism 26d is in an unlocked state); however, when dispensing button 26b is actuated, locking mechanism 26d is engaged to lock electronics unit 27 and dose knob 26a to one another such that electronics unit 27 and dose knob 26a rotate together as they translate into body 22 upon actuation of dose dispensing mechanism 24 to inject the selected dose.

The rotation of the dose knob 26a (and electronics unit 27) during actuation drives (direct or indirect) rotation of drive screw 26c which rides within a nut 26e which is fixed to body 22 of pen 20. In this manner, rotation of drive screw 26c also results in translation of drive screw 26c (due to the pitched threading of drive screw 26c) towards medicine cartridge 23 to thereby drive piston 23b through vial body 23a to expel medicine from medicine cartridge 23 for injection into the user. The extent to which dose knob 26a extends from body 22 of pen 20 prior to actuation (which corresponds to the selected dose to be injected) defines the maximum amount of rotation of dose knob 26a and, thus, drive screw 26c during actuation; as such, the amount of medicine expelled from medicine cartridge 23 during actuation cannot exceed the selected dose amount.

Operations monitoring mechanism 28 of pen 20 may include a rotary encoder 28a having a first part 28b rotationally fixed relative to body 22 of pen 20 and a second part 28c rotationally fixed relative to drive screw 26c such that relative rotation between the first and second parts 28b, 28c (which, in turn, is indicative of rotation of drive screw 26c relative to body 22 during dose dispensing), can be sensed and, thus, from which an amount of medicine dispensed can be determined (due to the proportional relationship between rotation of drive screw 26c and translation of piston 23b).

Alternatively or additionally, rotary encoder 28a may be configured to sense the amount of medicine dialed for dosing. In aspects, rotary encoder 28a is an electrical contact encoder including one or more contacts disposed on one of the parts 28b, 28c and a code wheel disposed on the other part 28b, 28c, although other configurations and/or types of encoders are also contemplated. Regardless of the particular type of encoder or other sensory components of operations monitoring mechanism 28, relative motion is measured and transmitted to electronics unit 27 for processing (e.g., determining an amount of medicine dispensed), storage (e.g., storing in memory the amount of medicine dispensed together with timestamp data) and/or transmission (e.g., transmitting the stored data to smartphone 30).

Figures 3A, 3B:
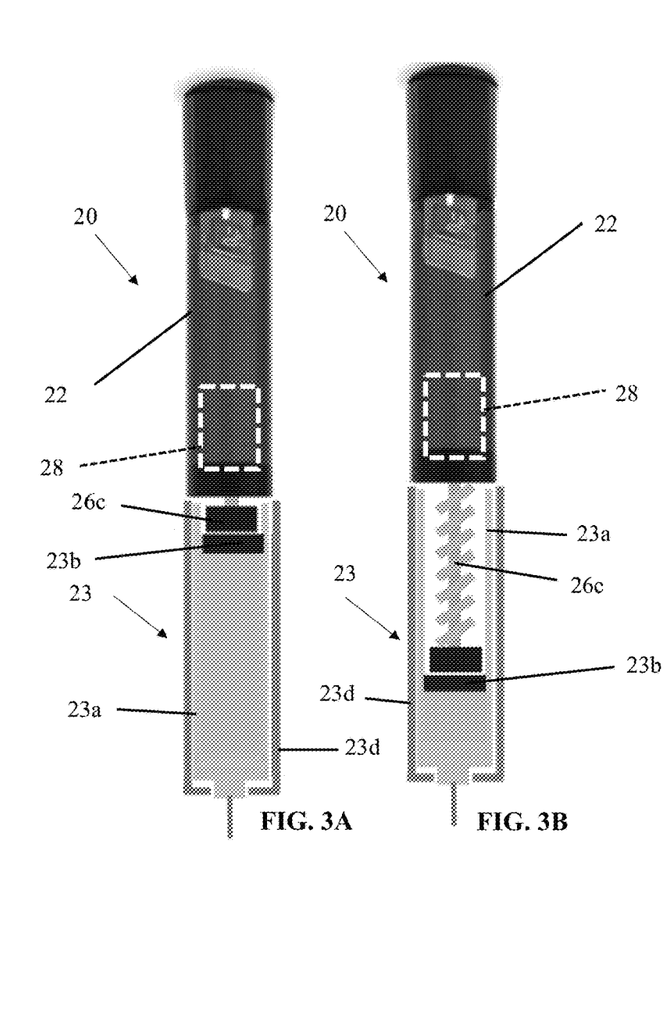
FIGS. 3A and 3B are side, partial longitudinal, cross-sectional views of the medicine injection pen of FIG. 1B with the medicine cartridge in a full condition and the medicine cartridge in a partially emptied condition, respectively.

Referring to FIGS. 3A and 3B, as noted above, operations monitoring mechanism 28 detects an amount of rotation of drive screw 26c, which is proportional to the distance drive screw 26c is translated. In the event that drive screw 26c is in abutment or close proximity to piston 23b prior to activation, the distance drive screw 26c is translated indicates the distance piston 23b is translated which, in turn, is proportional to the amount of medicine dispensed from vial body 23a. Thus, the amount of medicine dispensed can be calculated by detecting the amount of rotation of drive screw 26c (without having to know an absolute start or end position of drive screw 26c) and performing the appropriate calculations, e.g., according to the mathematical relationships between drive screw rotation and translation, drive screw translation and piston translation, and piston translation and medicine dispensed. This is the case, for example, in FIG. 3A, where pen 20 defines an initial configuration with drive screw 26c disposed in abutment or close proximity with piston 23b, which is disposed at the end of a substantially full cartridge. More specifically, upon one or more actuations from the initial position shown in FIG. 3A, to a subsequent position shown in FIG. 3B, the detected amount of rotation of drive screw 26c can be used to calculate the amount of medicine dispensed.

Figure 3C:
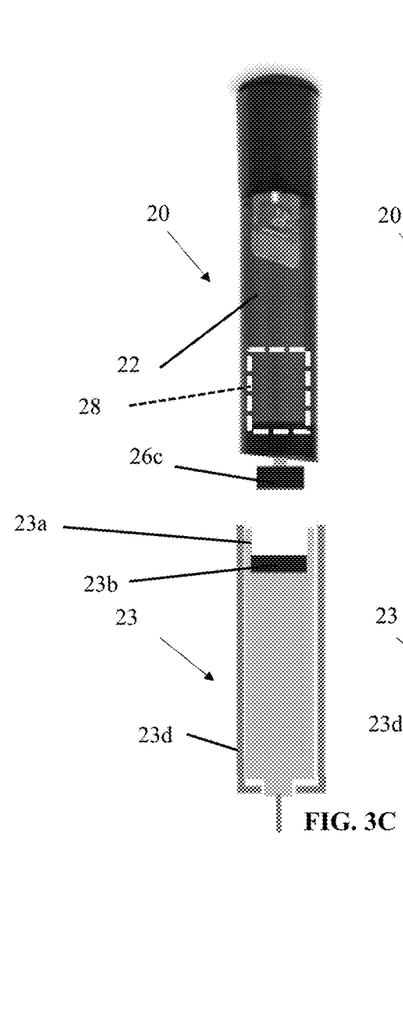
FIGS. 3C and 3D are side, partial longitudinal, cross-sectional views of the medicine injection pen of FIG. 1B with the cartridge housing (including a partially emptied cartridge of medicine therein) disengaged and engaged, respectively, with the body of the medicine injection pen.
Figure 3D:
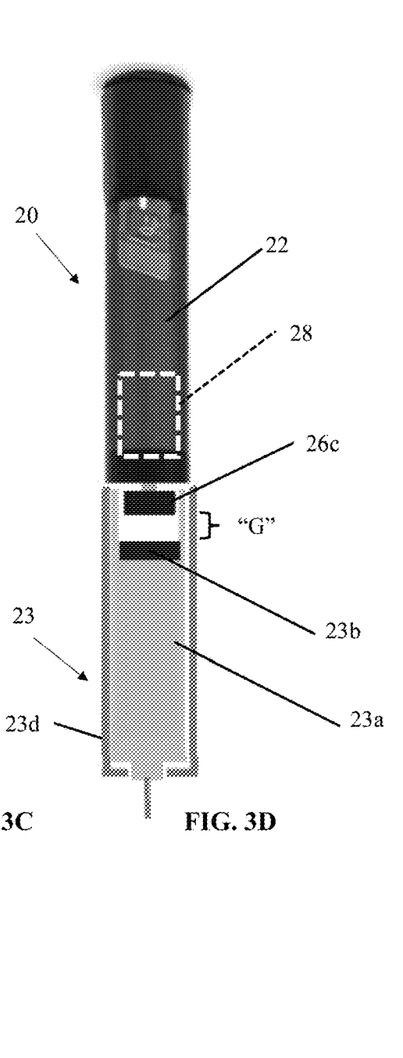

With additional reference to FIGS. 3C and 3D, in the event that drive screw 26c is not in abutment or close proximity to piston 23b prior to activation, the amount of medicine dispensed cannot be accurately detected as detailed above. This may be the case where pen 20 is not primed prior to activating pen 20 with a new medicine cartridge 23 installed; where cartridge housing 23d is not fully or properly engaged with body 22 of pen 20; where a different type, e.g., size, configuration, etc. of medicine cartridge 23 is utilized; where a partially emptied (i.e., not completely full) medicine cartridge 23 is engaged with body 22 of pen 20 (with drive screw 26c having been automatically or manually retracted upon disengagement or otherwise disposed out of position); and/or in other situations where drive screw 26c is not in abutment or close proximity to piston 23b prior to activation. Regardless of the reason, when drive screw 26c is not in abutment or close proximity to piston 23b prior to actuation but, rather, a gap "G" is defined between drive screw 26c and piston 23b, relying solely on detecting rotation of drive screw 26c cannot be utilized to accurately determine the amount of medicine dispensed but, instead, would result in over-counting of the amount dispensed because no medicine is being dispensed, despite drive screw 26c rotating and translating, as drive screw 26c traverses the gap "G" to a position in abutment or close proximity to piston 23b (after which translation of drive screw 26c is correlated with the amount of medicine dispensed and accurate determination of medicine dispensed can commence for that portion of travel of drive screw 26c).

In order to enable accurate determination of the amount of medicine dispensed, to adjust pen 20 such that accurate determination of the amount of medicine dispensed can be determined, to alert a user that adjustment to pen 20 is needed to enable accurate determination of the amount of medicine dispensed, and/or to indicate a possible error condition (e.g., incorrect engagement, incompatible cartridge, etc.), the presence of gap "G" and, in aspects the distance of gap "G," can be identified, compensated for, and/or eliminated. The proximity of and/or distance between other components of pen 20 can also be utilized for some or all of the above purposes. Various aspects and features of pen 20 to accomplish some or all of the above are detailed below with reference to FIGS. 4A-16, although it is understood that these aspects and features may similarly apply to any other suitable medicine injection device. To the extent consistent and not explicitly contradicted below, any of the aspects and features detailed below with respect to any of the configurations of FIGS. 4A-16 can be utilized, in whole or in part, in any suitable combination in a single medicine injection device to achieve a particular purpose.

Figure 4A:
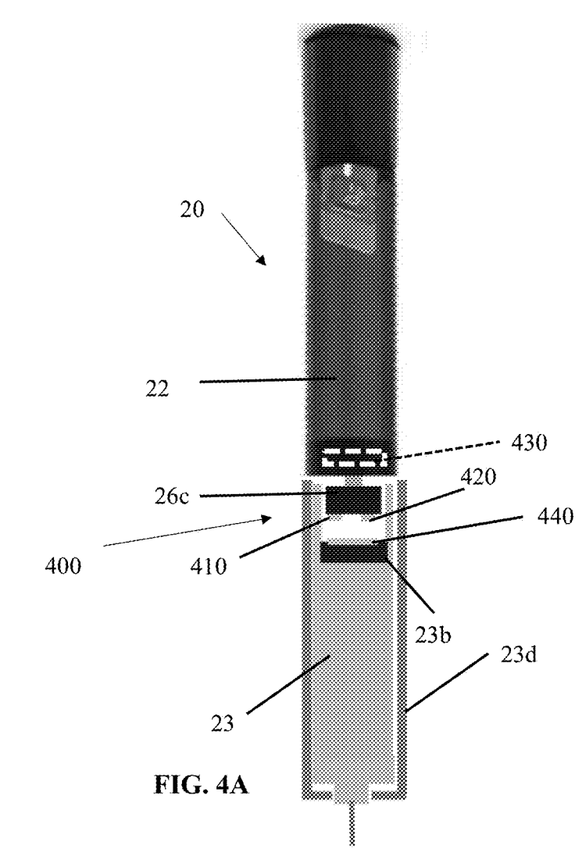
FIG. 4A is a side, partial longitudinal, cross-sectional view of the medicine injection pen of FIG. 1B including a detector in accordance with the present disclosure.
Figure 4B:
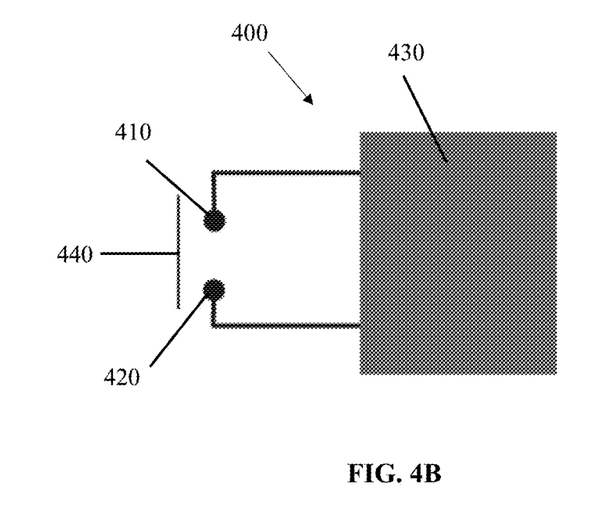
FIG. 4B is a schematic illustration of the detector of FIG. 4A.

Referring to FIGS. 4A and 4B, in aspects, pen 20 may include a detector 400 including pair of spaced-apart contacts 410, 420 disposed at the free end of drive screw 26c. Contacts 410, 420 are separately connected to a control circuit 430 of detector 400, e.g., a microcontroller, ASIC, or other suitable chip and/or circuit, capable of detecting a completed circuit upon electrical connection of contacts 410, 420 with one another. A contact plate 440 of detector 400 is disposed on piston 23b of medicine cartridge 23 and positioned such that, with drive screw 26c properly positioned and cartridge housing 23d properly engaged with body 22 of pen 20 with cartridge 23 therein, drive screw 26c is in abutment or close proximity to piston 23b such that contact plate 440 contacts each of contacts 410, 420, thereby completing an electrical circuit, as detected by control circuit 430. Control circuit 430 may then relay the same to electronics unit 27 (FIG. 2B) (or may be included in electronics unit 27 (FIG. 2B)) for output of an indicator notifying the user that pen 20 is properly assembled and ready for use. The output may be provided by pen 20, e.g., an audio tone from a speaker thereof, LED light activation, vibration, and/or may be communicated to health management application (FIGS. 1A and 1C) for providing a suitable indicator on the user interface thereof, e.g., an audio tone, visual icon, alert, message, etc.) Accordingly, the user can receive confirmation that cartridge 23 is properly installed and that there is no gap "G" (FIG. 3D) and, thus, that pen 20 is ready for use.

Figure 5A:
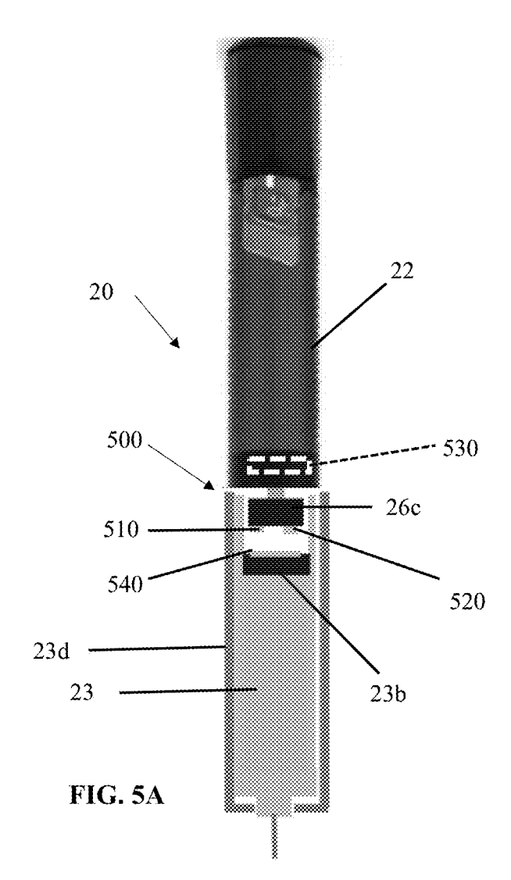
FIG. 5A is a side, partial longitudinal, cross-sectional view of the medicine injection pen of FIG. 1B including a detector and identifier in accordance with the present disclosure.
Figure 5B:
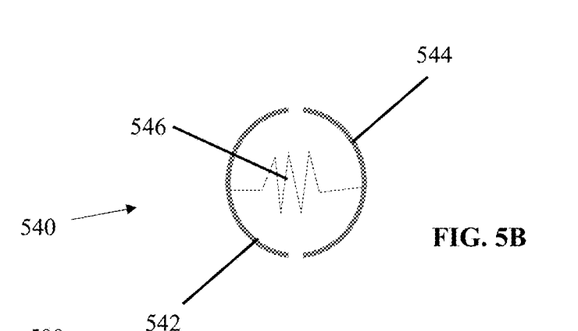
FIG. 5B is a schematic illustration of a contact assembly of the detector and identifier of FIG. 5A.
Figure 5C:
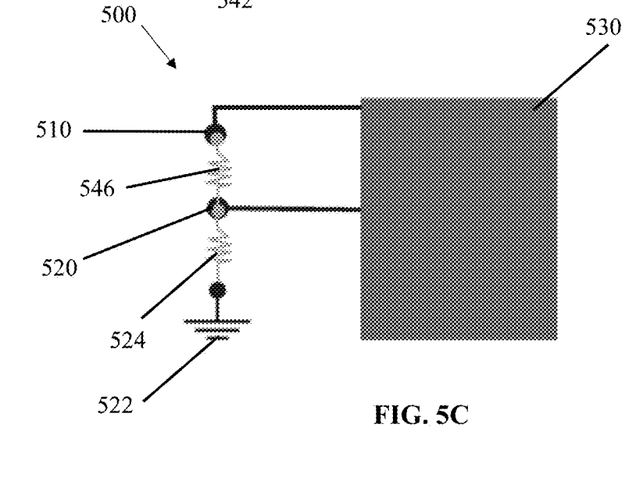
FIG. 5C is a schematic illustration of the detector and identifier of FIG. 5A.

With reference to FIGS. 5A-5C, in aspects, pen 20 may include a detector and identifier 500 including pair of spaced-apart contacts 510, 520 disposed at the free end of drive screw 26c. Contacts 510, 520 are separately connected to a control circuit 530 of detector and identifier 500, e.g., a microcontroller, ASIC, or other suitable chip and/or circuit, capable of detecting a completed circuit upon electrical connection of contacts 510, 520 with one another as well as an electrical parameter of the circuit, e.g., voltage, current, resistance, etc. Contact 520 may be connected to ground 522 with a resistor 524 therebetween.

A contact assembly 540 of detector and identifier 500 is disposed on piston 23b of medicine cartridge 23 and includes first and second contact plates 542, 544 connected via a resistor 546 and positioned such that, with drive screw 26c properly positioned and cartridge housing 23d properly engaged with body 22 of pen 20 with cartridge 23 therein, drive screw 26c is in abutment or close proximity to piston 23b such that contact plates 542, 544 contact contacts 510, 520, respectively, thereby completing an electrical circuit through resistor 546, as detected by control circuit 530. Control circuit 530 is further configured as a voltage divider circuit to enable determination of an electrical parameter, e.g., resistance across resistor 546. The resistance of resistor 546 may be selected to correspond to a particular batch, lot, manufacturer, manufacture date, medicine type, etc. associated with cartridge 23 to enable control circuit 530 to obtain this information. Control circuit 530 may then relay the detection of a completed circuit and the obtained information to electronics unit 27 (FIG. 2B) (or may be included in electronics unit 27 (FIG. 2B)) for output of an indicator notifying the user that pen 20 is properly assembled and ready for use, e.g., similarly as detailed above, and/or to provide the obtained information. Accordingly, the user can receive confirmation that cartridge 23 is properly installed and that there is no gap "G" (FIG. 3D) and, thus, that pen 20 is ready for use; the other information obtained may be utilized by health management application 40 (FIGS. 1A and 1C), may be associated with dose tracking data, and/or may be utilized in any other suitable manner.

Figure 6:
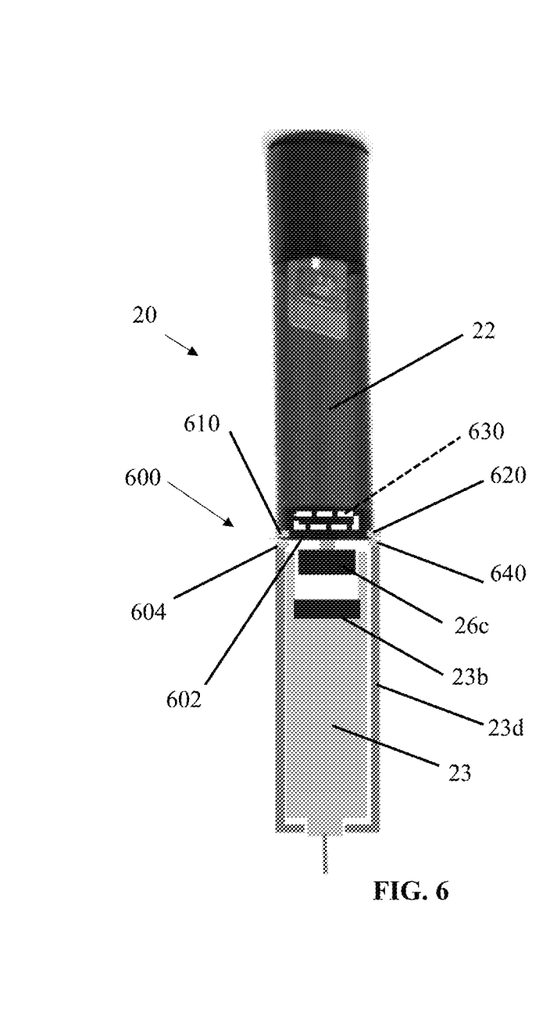
FIGS. 6-14 are side, partial longitudinal, cross-sectional views of the medicine injection pen of FIG. 1B including other detectors and/or identifiers in accordance with the present disclosure.

As illustrated in FIG. 6, in aspects, pen 20 may include a detector 600 including pair of spaced-apart contacts 610, 620 disposed on the outer periphery of body 22 of pen 20 adjacent engagement face 602 thereof or on engagement face 602. Engagement face 602 is configured to mate with a corresponding engagement face 604 of cartridge housing 23d upon engagement, e.g., threaded engagement, of cartridge housing 23d with body 22 of pen 20. Cartridge housing 23d includes a contact ring 640 of detector 600 disposed on or adjacent engagement face 604. Alternatively, contact ring 640 may be disposed on a face of cartridge 23.

Contacts 610, 620 are separately connected to a control circuit 630 (similar to control circuit 430 (FIGS. 4A-4B), control circuit 530 (FIGS. 5A-5C), or any other suitable control circuit) capable of detecting a completed circuit upon electrical connection of contacts 610, 620 with one another, e.g., via contact of contact ring 640 with each of contacts 610, 620, thus enabling output of an indicator notifying the user that pen 20 is properly assembled. Detector 600, however, does not detect the relative positioning of drive screw 26c or piston 23b.

Figure 7:
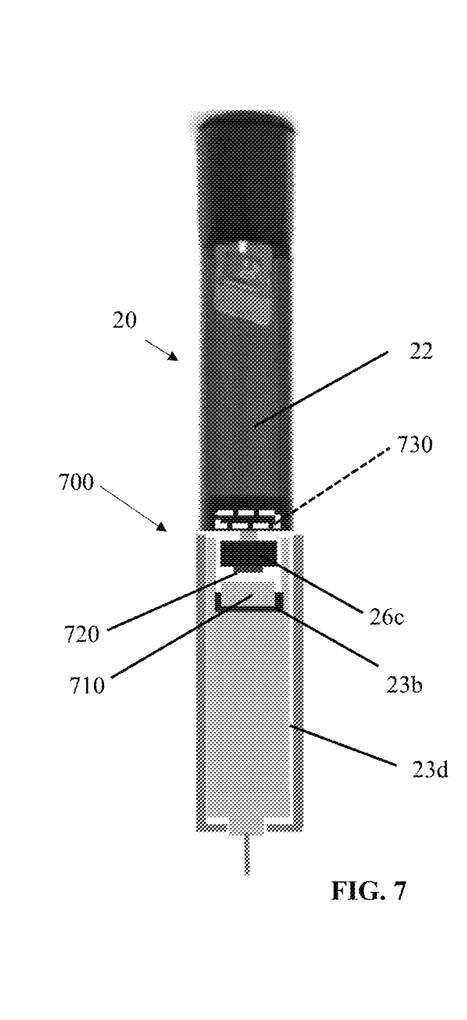
Figure 8:
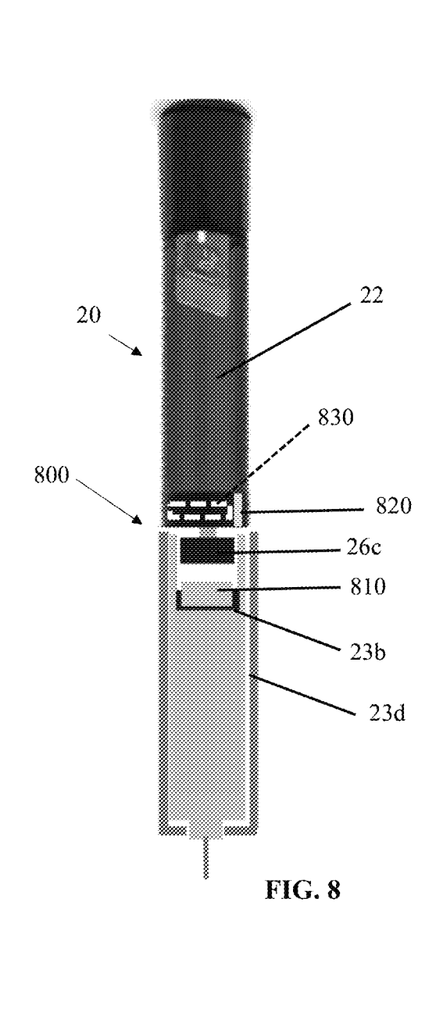

Turning to FIGS. 7 and 8, in aspects, pen 20 may include a detector 700 or 800 including a magnet 710 or 810 disposed on piston 23b and a magnet sensor 720 or 820 (e.g., a TMR magnet sensor or other suitable magnet sensor) disposed on the free end of drive screw 26c or within body 22 towards the engagement end thereof, respectively. A control circuit 730, 830 of detector 700, 800, e.g., a microcontroller, ASIC, or other suitable chip and/or circuit, is capable of detecting when magnet 710, 810 is within range of magnet sensor 720, 820, respectively, and/or a proximity of magnet 710, 810 from the respective magnet sensor 720, 820. Based on this information, control circuit 730 can be determine whether drive screw 26c and piston 23b are sufficiently approximated and/or the distance therebetween can be determined (see FIG. 7); and control circuit 830 can determine whether body 22 and piston 23b are sufficiently approximated and/or the distance therebetween can be determined (FIG. 8). Thus, a suitable output can be provided (e.g., as detailed above) when cartridge housing 23d is properly engaged with body 22 of pen 20 and/or when drive screw 26c is in abutment or close proximity to piston 23b.

Figure 9:
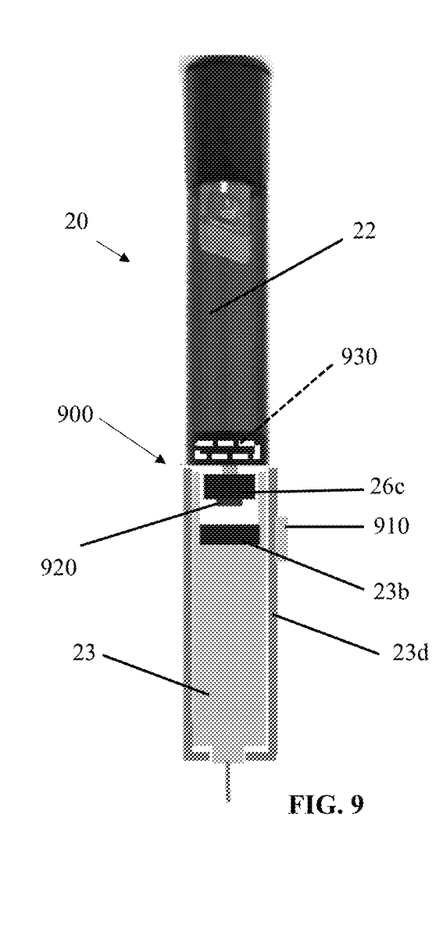

With reference to FIG. 9, in aspects, pen 20 may include a detector and identifier 900 including a magnet 910 disposed on cartridge housing 23d (or, alternatively, on cartridge 23) and a magnet sensor 920 (e.g., a TMR magnet sensor or other suitable magnet sensor) disposed on the free end of drive screw 26c (as shown) or within body 22 towards the engagement end thereof (see FIG. 8). Detector 900 further includes a control circuit 930 and may otherwise be configured similar to detectors 700, 800 (FIGS. 7 and 8). Other suitable positions for magnet 910 and magnet sensor 920 are also contemplated. The orientation, position, number, and/or strength of magnet 910 may provide information detectable by magnet sensor 920 that can correspond to information about cartridge 23 such as, for example, batch, lot, manufacturer, manufacture date, medicine type, etc. Control circuit 930 may thus obtain this information and output the same, similarly as detailed above with respect to detector and identifier 600 (FIG. 6). In aspects where an identifier is provided, a look-up table or other suitable key may be provided to enable determination of the cartridge information based on the sensed information.

In aspects, a sensor such as, for example, a mechanical switch or other suitable binary (ON/OFF) sensor, may be disposed on the free end of drive screw 26c and/or on piston 23b to enable detection of sufficient contact between the free end of drive screw 26c and piston 23b. Thus, a suitable output can be provided (e.g., as detailed above) when drive screw 26c is in abutment with piston 23b. Further, such a switch or other suitable sensor to detect the contacting or abutting position between drive screw 26c and piston 23b can be utilized to establish an absolute or reference position from which another sensor, e.g., the encoder of operations monitoring mechanism 28, is able to determine relative position from the absolute or reference position. Likewise, any of the other detectors of the present disclosure may be utilized in combination with one another to provide but absolute and relative positioning and/or for other purposes.

Figure 10:
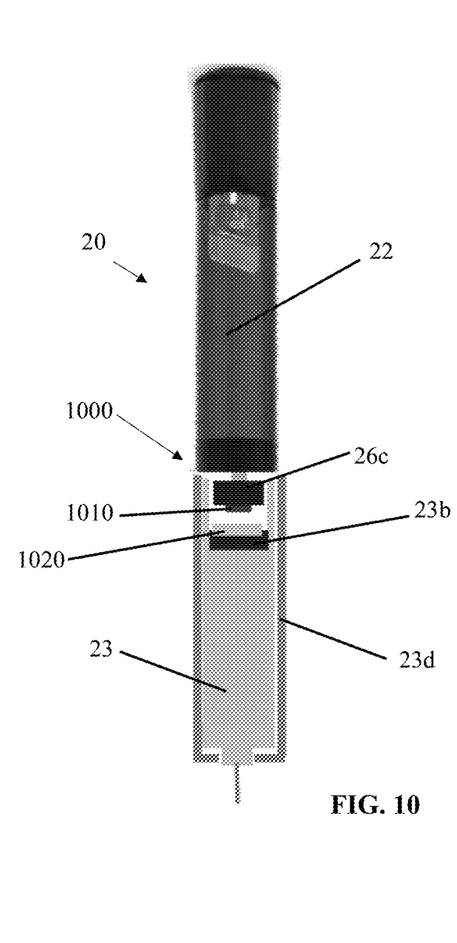
Figure 11:
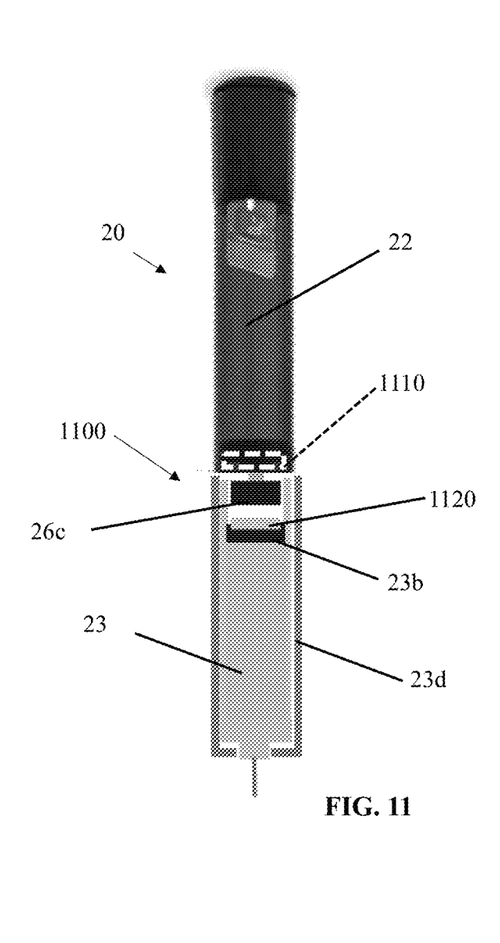

Referring to FIGS. 10 and 11, in aspects, pen 20 may include a detector 1000 or 1100 including an RFID reader 1010 or NFC reader 1110 disposed on the free end of drive screw 26c and an RFID tag 1020 or NFC tag 1120, respectively, disposed on piston 23b. Alternatively, the readers 1010, 1110 may be disposed on body 22 and/or the tags 1020, 1120 may be disposed on cartridge housing 23d or cartridge 23. Readers 1010, 1110 are capable of detecting when magnet tags 1020, 1120 are within range of readers 1010, 1110. Based on this information, it can be determined whether drive screw 26c and piston 23b are sufficiently approximated such that a suitable output can be provided (e.g., as detailed above). Information may also be communicated via the RFID or NFC connection such as, for example, batch, lot, manufacturer, manufacture date, medicine type, etc.

Figure 12:
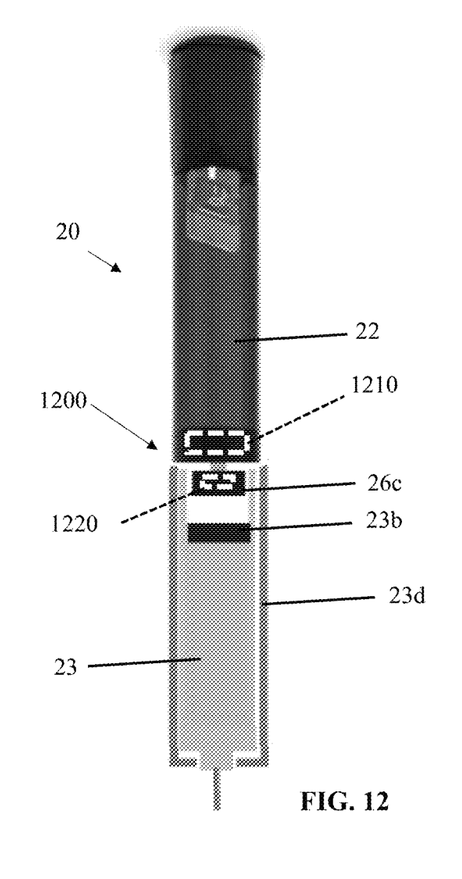

As shown in FIG. 12, in aspects, pen 20 may include a detector 1200 including a proximity sensor 1210 disposed on drive screw 26c or body 22 and configured to sense whether a detection element 1220 is sufficiently approximated relative to proximity sensor 1210 and/or a distance between detection element 1220 and proximity sensor 1210. Detection element 1220 may be disposed on drive screw 26c, piston 23b, cartridge 23, or cartridge housing 23d and may be a distinct element disposed thereon or a portion of the component itself. Proximity sensor 1210 may be configured as an optical sensor configured to optically sense proximity and/or distance, a hall effect sensor, a capacitive sensor, a mechanical switch, and/or other suitable sensor configured to sense proximity and/or distance. The proximity and/or distance information may be used similarly as any of the aspects above or in any other suitable manner.

Figure 13:
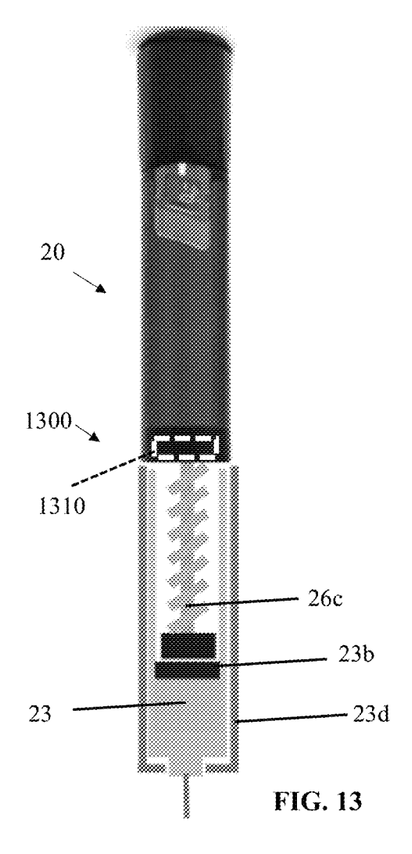

Turning to FIG. 13, in aspects, pen 20 includes a detector 1300 including a force sensor 1310, e.g., a linear force sensor and/or a torque sensor, associated with the translation and/or rotation of drive screw 26c. More specifically, force sensor 1310 is configured to distinguish between the force required to move drive screw 26c freely and the force required to move drive screw 26c to urge piston 23b to dispense medicine from cartridge 23. In this manner, in the event there is a gap "G" (FIG. 3D) defined between drive screw 26c and piston 23b prior to activation, any sensed rotation of drive screw 26c while drive screw 26c is moving freely can be disregarded and; thus, only the rotation of drive screw 26c while drive screw 26c urges piston 23b to dispense medicine from cartridge 23 is counted, thereby ensuring accurate dose detection. Alternatively or additionally, force sensor 1310 may be configured to determine once drive screw 26c contacts piston 23b to enable an indication to be provided that pen 20 is sufficiently primed.

Force sensor 1310 may, in addition or as an alternative to the above, be configured to sense an end stop, e.g., as detected by a force spike, when drive screw 26c is fully retracted, thus enabling determination and tracking of the absolute position of drive screw 26c, e.g., to facilitate priming, moving drive screw 26c into the appropriate position, and/or for other purposes. Knowing the absolute position of drive screw 26c can further enable, for example, determination of the amount of medicine remaining in cartridge 23, e.g., using the absolute position of drive screw 26c and detecting contact of drive screw 26c with piston 23b according to any of the aspects detailed above.

Figure 14:
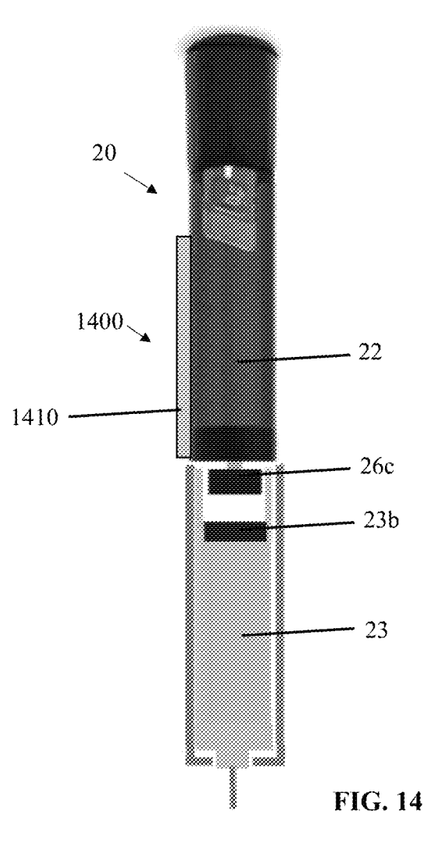

Referring to FIG. 14, in aspects, pen 20 includes a detector 1400 having a force sensor 1410 extending along (exteriorly or interiorly) body 22 of pen 20. Force sensor 1410 enables the sensing of force acting thereon which can be utilized, for example, when pen 20 is placed, with force sensor 1410 down, on a support surface, e.g., a desk, table, floor, etc., to determine a force associated with the weight of pen 20. Based on the force sensed, the weight of pen 20 can be determined and, subtracting static weights, the weight of the medicine in cartridge 23 can be determined. Thus, an amount of medicine in cartridge 23 and, correspondingly, a position of piston 23b, can be determined to enable, for example, adjustment of drive screw 26c, a recommended priming, adjusted calculation of an amount of medicine dispensed, etc.

Figure 15:
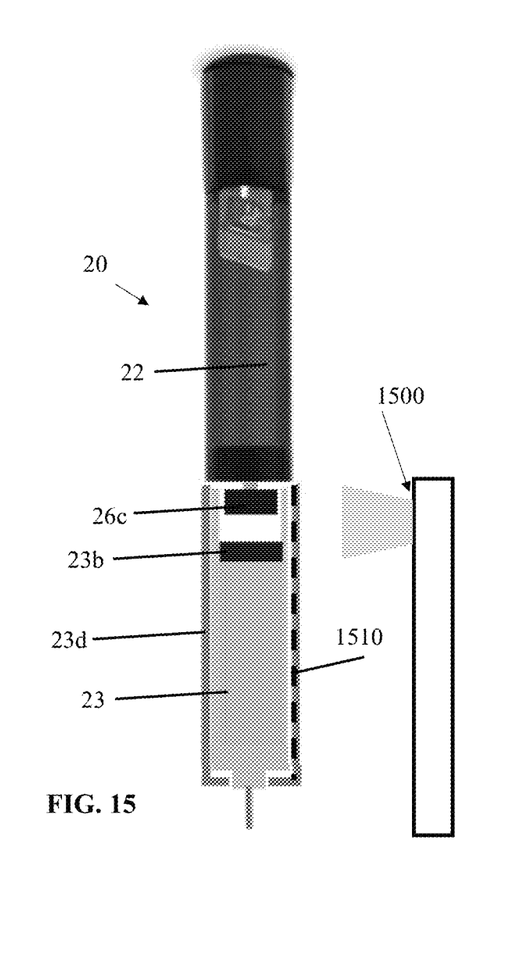
FIG. 15 is a side, partial longitudinal, cross-sectional view of the medicine injection pen of FIG. 1B and an image capture device positioned to capture an image of the medicine injection pen.

With reference to FIG. 15, an image capture device 1500, e.g., a camera of smartphone 30 (see also FIG. 1A) may be utilized to capture an image of cartridge housing 23d when connected to body of pen 20 to enable image processing, e.g., using health management application 40 (FIGS. 1A and 1C), of the captured image to determine absolute and/or relative positioning of drive screw 26c and piston 23b. In aspects, markings 1510 (e.g., distinguishable location markings, ruler lines, indicia, markings for scaling purposes, etc.) may be provided on cartridge housing 23d (and additionally or alternatively on cartridge 23, drive screw 26c, and/or body 22) to facilitate the image processing. The determined absolute and/or relative positioning of drive screw 26c and piston 23b may be utilized similarly as any of the aspects detailed above or in any other suitable manner. As an alternative or in addition to determining positioning of drive screw 26c and piston 23b, the position of piston 23b relative to cartridge 23 may be determined.

Figure 16:
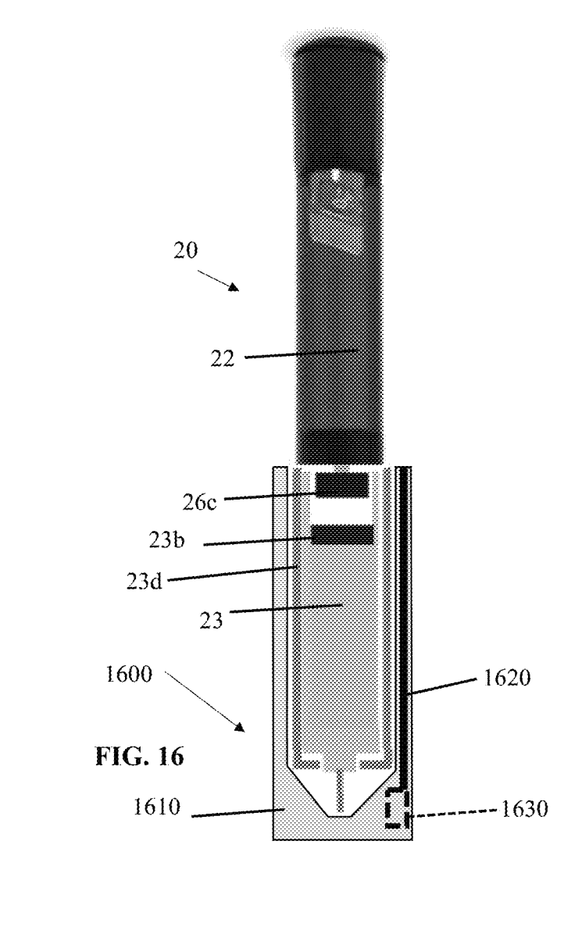
FIG. 16 is a side, partial longitudinal, cross-sectional view of the medicine injection pen of FIG. 1B including a cap having a detector.

FIG. 16 illustrates pen 20 including a sensing cap 1600 engaged therewith, e.g., replacing cap 21 (FIG. 1B). Sensing cap 1600 includes a body 1610 configured to engage cartridge housing 23d, e.g., to protect the injection end of pen 20, and to extend along and enclose at least a portion of a length thereof. Sensing cap 1600 further includes at least one sensor 1620 configured to sense proximity, an absolute position, and/or a relative position of drive screw 26c and/or piston 23b. Sensor 1620 may be configured similar to any of the other sensors detailed above or in any other suitable manner and may be configured to sense a portion of drive screw 26c and/or piston 23b or a detection component associated therewith. Sensing cap 1600 further includes a control circuit 1630 configured to communicate the information sensor by sensor 1620 to, for example, electronics unit 27 (FIGS. 1B and 2B) of pen 20 and/or health management application 40 via wireless communication or in any other suitable manner.

It is noted that, although detailed hereinabove with respect to durable pens wherein the cartridge is refilled and/or replaced plural times throughout the life of the pen, the present disclosure is equally applicable for use with disposable pens where the cartridge is not refillable or replaceable. That is, while position determination in durable pens is important each time the cartridge is replaced, for example, to ensure that the dose determination is accurate, disposable pens may also benefit from an absolute or initial position determination, e.g., at the completion of manufacturing, which is then stored in memory to as an absolute, initial, or reference position from which the encoder or other operations monitoring mechanism can measure change, similarly as detailed above.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A medicine injection pen, comprising:
   a body;
   a drive member disposed within the body and configured to move relative to the body upon actuation of the drive member;
   a cartridge housing releasably engageable with the body and configured to retain a medicine cartridge therein, the medicine cartridge configured to retain a liquid medicine therein and including a piston configured to slide within the medicine cartridge, wherein the drive member is configured to move relative to the body upon actuation thereof to urge the piston to slide within the medicine cartridge to thereby dispense at least some of the liquid medicine through a dispensing end of the medicine cartridge;
   at least one sensor configured to sense movement of the drive member relative to the body upon actuation of the drive member to enable determination of an amount of the liquid medicine dispensed based on the sensed movement; and
   at least one detector configured to measure a gap value between the drive member and the piston.

2. The medicine injection pen according to claim 1, wherein the at least one detector is configured to measure the gap value by measuring a distance between the drive member and the piston.

3. The medicine injection pen according to claim 1, wherein the at least one detector is configured to measure the gap value based at least in part on a force required to move the drive member.

4. The medicine injection pen according to claim 1, wherein the at least one detector is configured to measure the gap value based at least in part on a position of the piston.

5. The medicine injection pen according to claim 4, wherein the position of the piston is determined relative to at least one of: the body, the drive member, or the medicine cartridge.

6. The medicine injection pen according to claim 1, wherein the detector includes at least one of: a contact sensor, a magnet sensor, an optical sensor, a proximity sensor, a force sensor, an RFID sensor, or an NFC sensor.

7. The medicine injection pen according to claim 1, wherein the drive member is a drive screw configured to rotate and translate relative to the body to urge the piston to slide.

8. The medicine injection pen according to claim 7, wherein the at least one sensor is configured to sense rotation of the drive screw to enable determination of the amount of the liquid medicine dispensed.

9. The medicine injection pen according to claim 1, further comprising an electronics unit configured to output an indication based upon the gap value measured.

10. The medicine injection pen according to claim 9, wherein the indication indicates at least one of: that the pen is ready for use, that the pen requires priming, that the pen requires adjustment, or that there is an error.

11. The medicine injection pen according to claim 1, further comprising an electronics unit configured to determine the amount of the liquid medicine dispensed based on the sensed movement.

12. The medicine injection pen according to claim 11, wherein the electronics unit is configured to determine the amount of the liquid medicine dispensed based on the sensed movement and the gap value.

13. The medicine injection pen according to claim 1, wherein the at least one sensor is an encoder.

14. The medicine injection pen according to claim 1, wherein the detector is further configured to detect information relating to the medicine cartridge.

15. A medicine injection pen, comprising:
   a body;
   a drive member disposed within the body and configured to move relative to the body upon actuation of the drive member;
   a cartridge housing releasably engageable with the body and configured to retain a medicine cartridge therein, the medicine cartridge configured to retain a liquid medicine therein and including a piston configured to slide within the medicine cartridge, wherein the drive member is configured to move relative to the body upon actuation thereof to urge the piston to slide within the medicine cartridge to thereby dispense at least some of the liquid medicine through a dispensing end of the medicine cartridge;
   at least one sensor configured to sense movement of the drive member relative to the body upon actuation of the drive member to enable determination of an amount of the liquid medicine dispensed based on the sensed movement; and
   at least one detector configured to detect a gap between the drive member and the piston, wherein the at least one detector is configured to detect the gap by determining a position of the piston based on an amount of the liquid medicine in the medicine cartridge.

* * * * *